United States Patent [19] [11] 4,226,675
Lewis et al. [45] Oct. 7, 1980

[54] METHOD AND APPARATUS FOR MONITORING AND MEASURING A GAS

[75] Inventors: Gary W. Lewis, Fountain Valley; Alfred D. Robinson, El Monte, both of Calif.

[73] Assignee: Comsip Delphi, Inc., El Monte, Calif.

[21] Appl. No.: 799,307

[22] Filed: May 23, 1977

[51] Int. Cl.² .................... G21C 17/00; G01N 31/12
[52] U.S. Cl. ................... 176/19 R; 176/37; 23/232 E
[58] Field of Search .......... 176/19 R, 37, 38; 73/27 R; 23/232 E, 254 E

[56] References Cited

U.S. PATENT DOCUMENTS

| | | | |
|---|---|---|---|
| 1,893,490 | 1/1933 | Beekley | 23/232 E |
| 2,149,441 | 3/1939 | Jacobson | 23/232 E |
| 2,633,737 | 4/1953 | Richardson | 73/27 R |
| 2,698,223 | 12/1954 | Richardson | 73/27 R |
| 2,905,536 | 9/1959 | Emmett et al. | 23/232 E |
| 2,916,358 | 12/1959 | Valentine et al. | 23/232 E |
| 3,028,327 | 4/1962 | Weeks | 176/37 |
| 3,097,518 | 7/1963 | Taylor et al. | 73/27 R |
| 3,252,759 | 5/1966 | Simon | 73/27 R |
| 3,320,969 | 5/1967 | Gordon | 176/37 |
| 3,444,725 | 5/1969 | Chave | 176/37 |
| 3,549,327 | 12/1970 | Fergusson | 73/27 R |
| 3,558,283 | 1/1971 | Freeman et al. | 73/27 R |
| 3,594,127 | 7/1971 | Davis | 23/232 E |
| 3,606,790 | 9/1971 | Matsumoto et al. | 73/27 R |
| 3,756,069 | 9/1973 | Carswell, Jr. et al. | 73/27 R |
| 3,788,813 | 1/1974 | Busch | 176/19 LD |
| 3,890,100 | 6/1975 | Busch | 176/19 LD |
| 3,937,796 | 2/1976 | Bhan | 176/37 |
| 3,960,500 | 6/1976 | Ross et al. | 23/254 E |

FOREIGN PATENT DOCUMENTS 270494  5/1964  Australia .............................. 73/27 R

OTHER PUBLICATIONS

Journal of Nuclear Science and Technology, 10 [2] pp. 118-124 (2/73).

Primary Examiner—Stephen C. Bentley
Assistant Examiner—S. A. Cangialosi
Attorney, Agent, or Firm—Edward J. DaRin

[57] ABSTRACT

Method and apparatus for monitoring and signalling the quantity of a known gas, or gases, in a gas mixture. The monitoring system is particularly adapted to continuously sense the quantity of hydrogen or oxygen in the containment gas mixture for a nuclear reactor electrical power generator. The monitoring system utilizes thermal conductivity gas measuring cells arranged in an electrical bridge network along with a catalytic reactor for modifying the constituency of the containment gas mixture undergoing measurement to provide the signal representative of the changes in constituency of the containment gas mixture at the power generating site.

11 Claims, 5 Drawing Figures

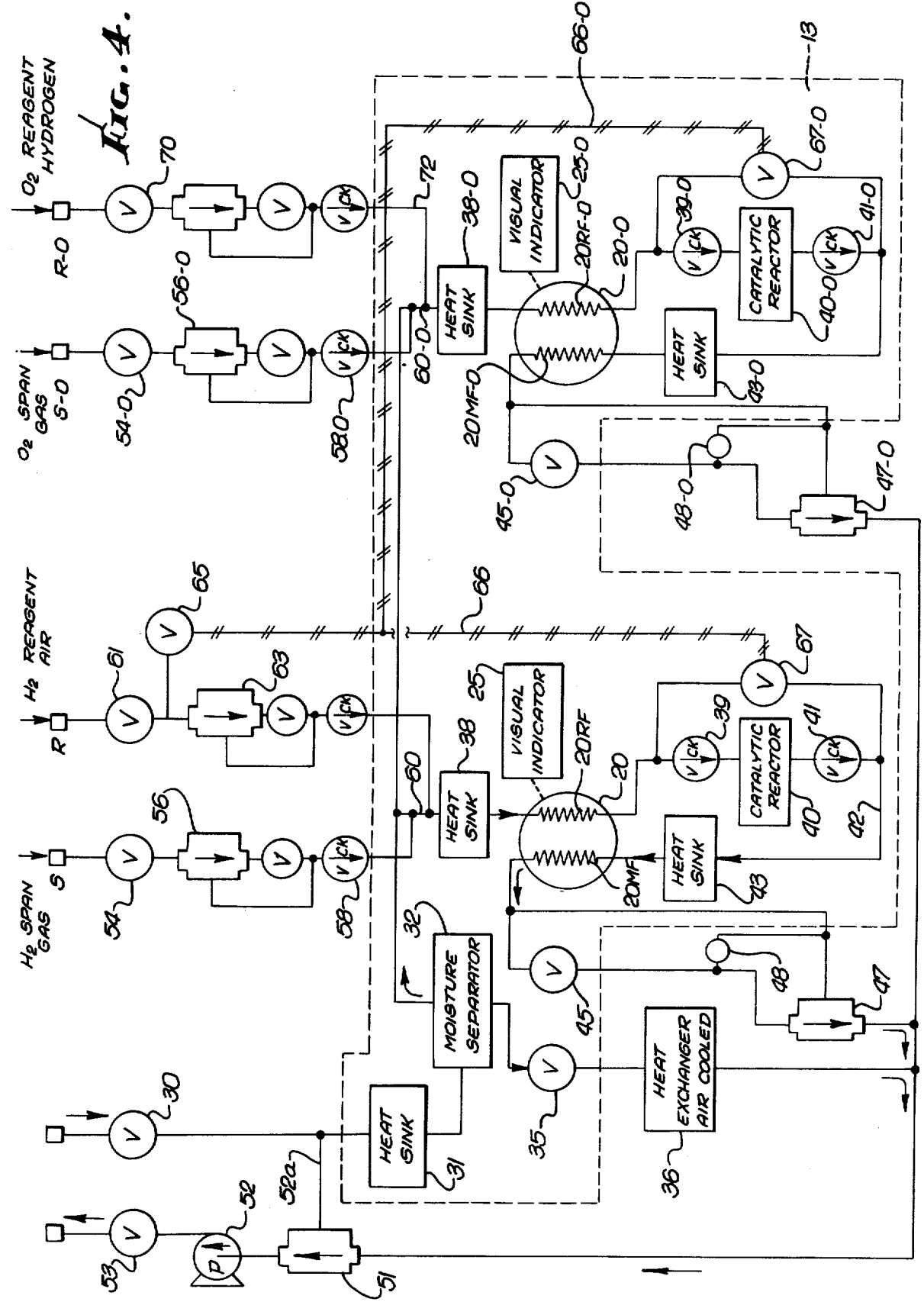

METHOD AND APPARATUS FOR MONITORING AND MEASURING A GAS

PRIOR ART AND SUMMARY OF THE INVENTION

This invention relates to a method and apparatus for measuring the quantity of a gas in a gas mixture such as the amount of hydrogen or oxygen in the containment gas mixture for a nuclear reactor electrical power generator.

The nuclear reactor electrical power generators that are constructed in this country are always being examined from a safety standpoint for preventing accidents of all types. Most of the nuclear power electrical generators that are in operation or are being built in this country are water cooled. The most catastrophic event, from a safety standpoint, that could occur in these reactors would be an accident that results in the complete loss of coolant to the reactor. Such a loss of coolant accident would arise from a complete breakdown in the cooling water system resulting from a complete break in one or more of the main coolant water lines. This could cause all pressure and water to the reactor to be lost. To appreciate the nature of this type of accident, it should be understood that the nuclear reactor electrical power generator and its associated equipment is generally housed in a large containment vessel which may appear as a large sphere or tank at the power generating plant site. The reactor housing is usually filled with a gas mixture when a loss of coolant accident occurs. This containment gas usually surrounds the reactor equipment within the housing or sphere and is at ambient temperature. When a loss of coolant accident occurs, the containment gas is rapidly filled with steam and water from the coolant system. When the coolant is removed from the nuclear reactor generator, the core melts releasing radioactive waste into the containment gas and results in the melted core being dumped in the water at the bottom of the containment. The radioactive wastes cause some of the water to become disassociated into hydrogen and oxygen. In addition, the hot zirconium from the fuel rod clading reacts with the water to release more hydrogen. This leaves the containment filled with a possibly explosive mixture laced with radioactivity and at a pressure of 60 to 70 pounds per square inch and a temperature of 300 to 360 degrees Fahrenheit. In order to keep this potential for public disaster from being realized, it is necessary to monitor the containment for hydrogen and oxygen and if excessive amounts are detected, more steam or nitrogen are added to keep the gas mixture below the explosive limit. The gases can be then run through a catalyst bed to recombine the hydrogen and the oxygen to water. As a result of the rapid and extreme changes in pressure, temperature and composition, the conventional sensors employed for hydrogen and oxygen sensings are complicated to apply. Of the known gas sensors, only a thermal conductivity sensor appears to be theoretically insensitive to pressure and temperature and is therefore capable of being operated at the conditions that prevail in the containment before, during and after a loss of coolant accident. Accordingly, at the present time there is a need for an improved method and apparatus for measuring the quantity of a gas such as hydrogen or oxygen in a gas mixture comprising the containment gases for a nuclear reactor electrical power generator.

The present invention provides an improved method and apparatus for measuring the quantity of a gas such as hydrogen and oxygen in the containment gas for a nuclear reactor electrical power generator such as a boiling water reactor or a pressurized water reactor that meets the present day governmental requirements for such monitors. The gas monitor of the present invention provides for the continuous measurement, without attention, of hydrogen and/or oxygen in the containment gas independent of variations in temperature, pressure and steam concentration within certain prescribed ranges and producing readings in volume percentage measurements. The method and apparatus incorporates a measuring cell in the form of a thermal conductivity cell which is not affected by vibration or radiation and is operable at elevated temperatures. The type of thermal conductivity cell utilized has a reference cell section and a measuring cell section arranged with a catalytic reactor in the path of the gas sample to be measured as it is conveyed through one cell unmodified and through the other cell section as modified by the catalytic reactor.

In addition, the two thermal conductivity cell sections and the catalytic reactor are maintained at the same pressure thereby allowing the measurements to be unaffected by the source gas pressure or the pressure of the containment gas. The measurements are accomplished through the use of a reagent gas selected on the basis of the gas to be measured from the containment gas mixture. If it is desired to measure the oxygen content of the containment gas, hydrogen must be added to the containment gas undergoing measurement in an excessive amount. Similarly, an excessive amount of oxygen gas as the reagent must be added if the hydrogen gas content of the containment gas is to be measured. The excessive amounts of reagent gas are added to assure that the selected gas undergoing measurement is completely reacted out of the containment gas mixture. A constant mass flow of all the gases, containment gas sample, hydrogen reagent gas and oxygen reagent gas are all controlled and maintained at a constant for proper calibration of the measuring system. The constant mass flow of the gases is assured through the utilization of a heated compartment for housing the measuring cell and the catalytic reactor and which compartment is maintained at a temperature to prevent condensation of the steam in the gas sample. A flow control valve is also arranged in the heated compartment for controlling the flow of the gas sample after measurement and maintaining a substantially constant mass flow for measuring purposes. The thermal conductivity type of measuring cell employed in the monitoring system has been proven to be an extremely reliable measuring device. The gas, or gases, mixed in the gas sample have known thermal conductivities and the variations in composite thermal conductivity can be accurately determined. The measurement of hydrogen in the presence of nitrogen, oxygen and water vapor is possible by the thermal conductivity cell since the thermal conductivity of hydrogen is approximately seven times higher than nitrogen, oxygen or water vapor which have nearly identical thermal conductivities at certain temperatures. The thermal conductivity measuring cell is arranged in an electrical bridge network, the output of which indicates the change in sample constituents due to the catalytic reaction and thereby the quantity of the preselected gas in the containment gas.

From a method standpoint, the method comprehends measuring the quantity of gas in a gas mixture including the steps of providing a source of gas having a mixture of known gases therein and subject to rapid and extreme changes in pressure, temperature and composition. The steps include arranging a thermal conductivity measuring cell in an electrical bridge circuit with the measuring cell comprising two self-heating filaments in individual cavities for detecting any difference in heat conductivity of the gas conveyed past the filaments for signalling any differences in gas composition. The gas from the source is heated to a preselected temperature to prevent the condensation of any steam that may be mixed in with the gas from the source prior to its application to the measuring cell. The excessive amount of the reagent gas, hydrogen or oxygen, is added to the containment gas sample in accordance with the gas selected to be measured as described hereinabove. In a series arrangement of the measuring cell, the heated gas is then conveyed past one of the filaments of the measuring cell functioning as a reference. One of the gases from the heated gas mixture is removed after it has exited from the measuring cell and then conveyed past the other filament of the measuring cell. Any difference produced as a result of removal of the one gas from the gas sample as a result of being conveyed past the measuring filament of the thermal conductivity measure cell produces an unbalanced bridge condition and thereby signals the quantity of the preselected gas in the gas mixture. In the parallel arrangement of the measuring cell, each section of the cell is arranged in an individual arm with the gas sample flowing through each arm in a parallel flow path. The reference cell is solely arranged in one arm with the other arm having the catalytic reactor and the measuring cell section arranged in a serial flow path therein to thereby signal the quantity of the preselected gas in the gas mixture.

From an apparatus standpoint, the improvement for monitoring and signalling a quantity of preselected gas in mixture of gases comprises means for receiving a sample of gas to be monitored from a source, and means for heating the gas sample to a preselected temperature. Means for separating out a portion of the heated gas sample is provided along with thermal conductivity gas sensing means for measuring and signalling the quantity of a preselected known gas in the gas sample. Means for adding the selected reagent gas to the separated gas sample is provided. The apparatus includes means for conveying the separated portion of the heated gas along with the reagent gas to the sensing means for conveying it therethrough and catalytic reactor means arranged in the path of the gas exiting from the gas sensing means for altering one of the gas constituents in the heated gas. The apparatus includes means for conveying the gas mixture and reagent gas through the catalytic reactor means in either the aforementioned series or parallel relationship with the gas sensing means. The heating means for the system includes means for maintaining the gas sensing means and the catalytic reactor means at a preselected temperature to maintain the steam content in the gas. The gas emerging from the gas sensing means is conveyed from the sensing means along with the remaining portion of the gas sample to the source of gas after measurement.

These and other features of the present invention may be more fully appreciated when considered in the light of the following specification and drawings, in which.

Figure 2:
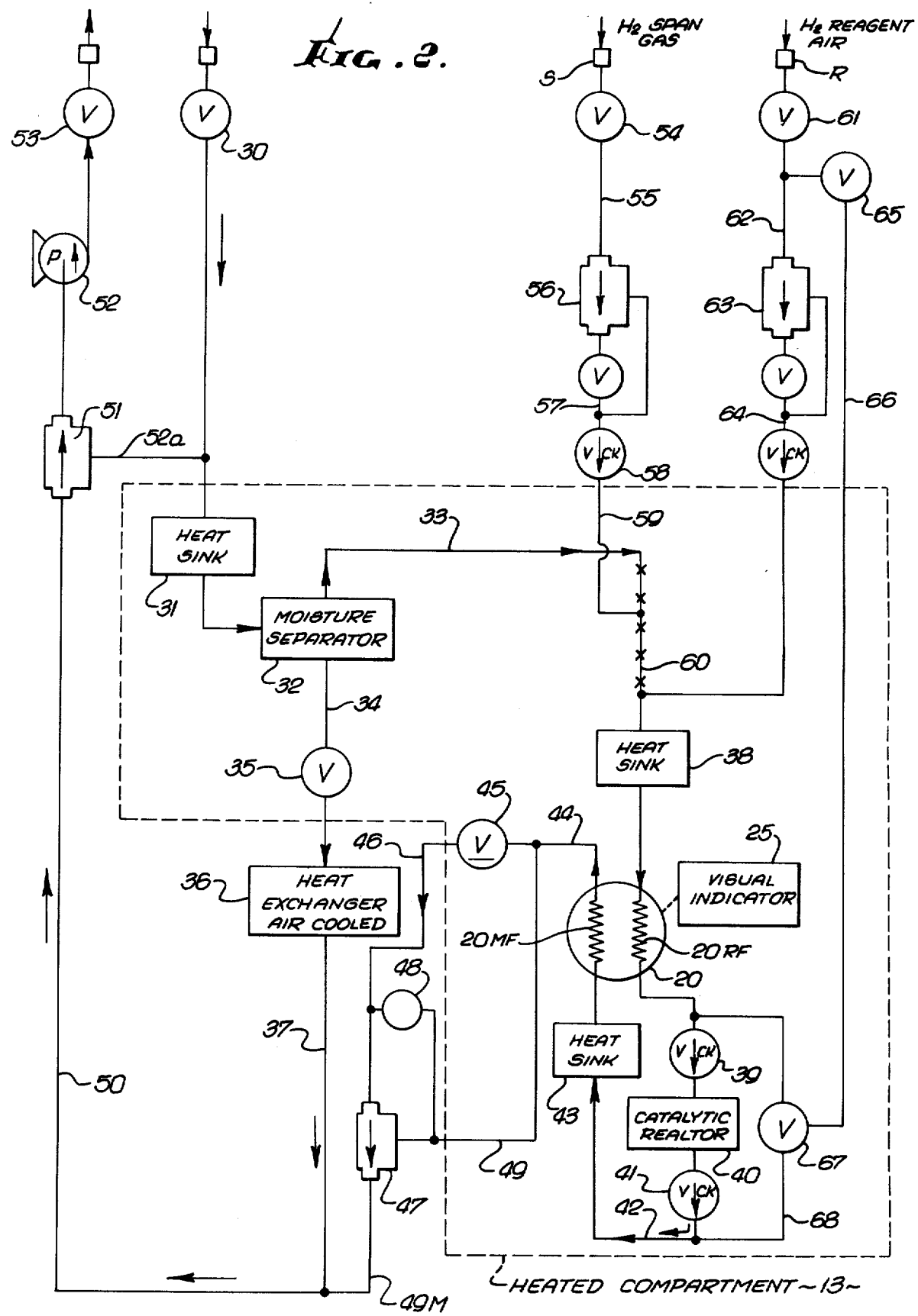
FIG. 2 is a diagrammatic piping and instrumentation illustration of the analyzing system of the present invention for analyzing a preselected gas, such as hydrogen contained in a gas sample with the two cell sections of the thermal conductivity cell arranged in a serial flow path.
Figure 5:
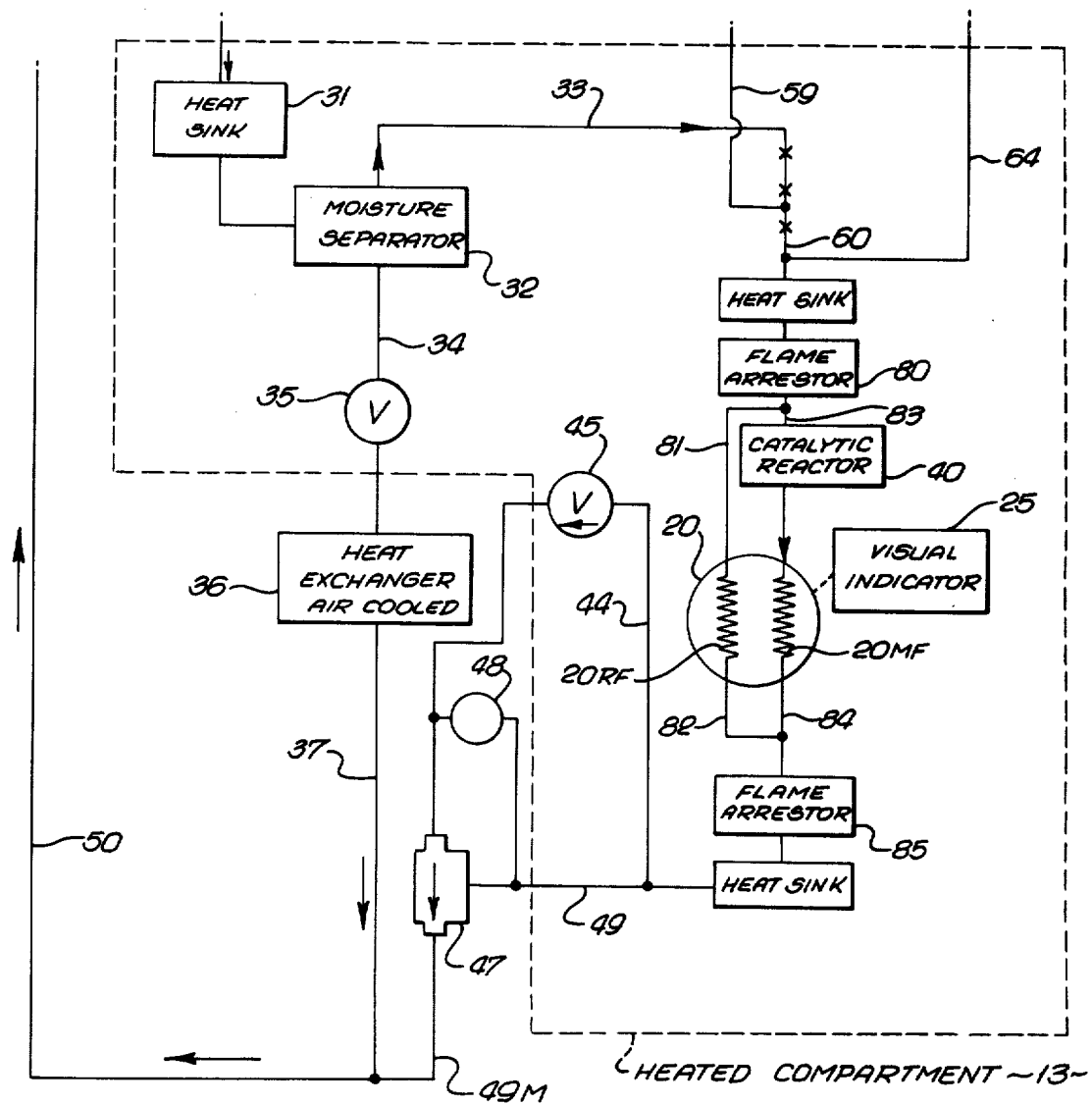

FIG. 4 is a diagrammatic piping and instrumentation illustration of the analyzing system of the present invention for analyzing both the hydrogen and oxygen content of the containment air of the pressure vessel; and FIG. 5 is a diagrammatic piping and instrumentation illustration of the measuring system portion of the analyzing system with the thermal conductivity cell sections arranged in a parallel flow path in a system as illustrated in FIG. 2.

Figure 1:
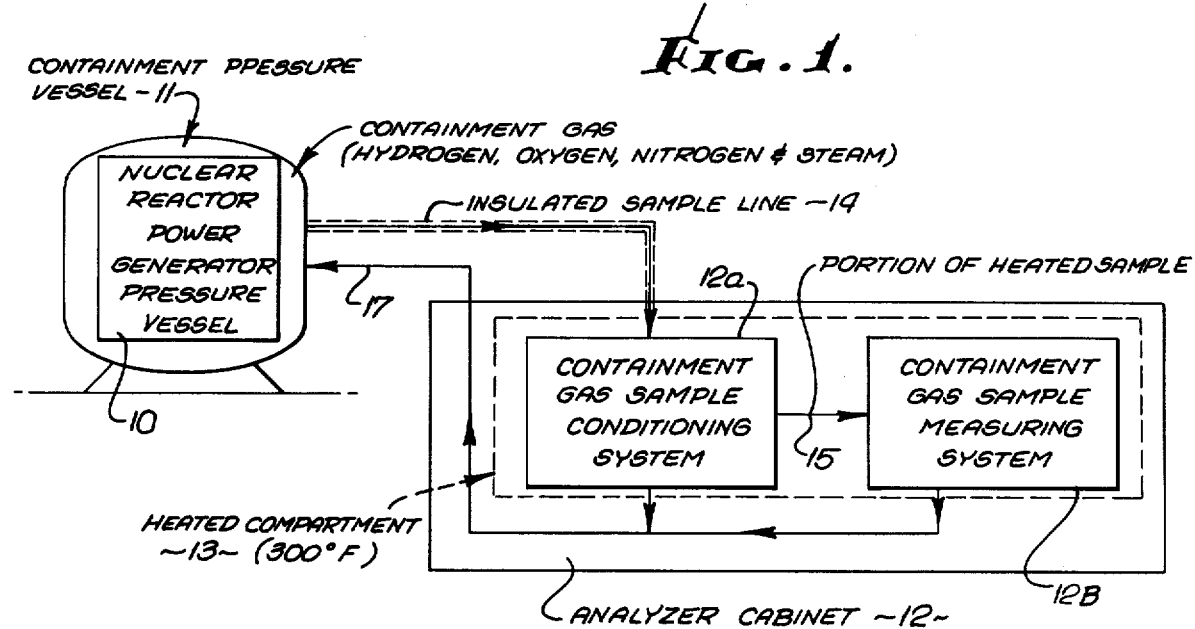
FIG. 1 is a schematic illustration of a nuclear reactor power generator vessel illustrating the gas analyzing system arranged therewith and embodying the present invention.

Now referring to the drawings, the method and apparatus for monitoring and measuring the quantity of preselected gases in the containment gas mixture of a containment pressure vessel for a nuclear reactor electrical power generator will be described. To better appreciate the nature of the invention, a general understanding of the manner in which a nuclear reactor power generator is usually housed will be briefly considered as illustrated in FIG. 1. The nuclear reactor power generator is usually housed in a pressure vessel identified as the block 10 in FIG. 1. The power generator 10 and its associated equipment is generally housed in a large containment vessel such as a sphere 11. The vessel 11 is constructed to permit individuals to enter the sphere, and walk around to examine reactor and associated equipment. The containment gases are considered to be the mixture of gases that surround the pressure vessel 10 and are completely enclosed within the sphere 11. The containment gases are considered to be the atmospheric air. Most nuclear reactors are water cooled and it is important that the coolant be maintained in an operative condition to prevent damage due to the loss of coolant or water to the reactor. The most catastrophic event in a nuclear power generator is a complete break in the water lines to the reactor whereby all the pressure and water is lost. When there is a loss of coolant to the reactor, the loss will rapidly introduce additional steam and water into the containment gas mixture from the cooling system. Within approximately thirty seconds after the loss of coolant to the reactor, the containment temperature will have gone from approximately 70 degrees Fahrenheit to 350 degrees Fahrenheit and the pressure will have gone up to 75 pounds per square inch of ambient from 15 pounds per square inch of ambient. This serious operating condition is normally signalled by a multiplicity of alarms for the safety of the operating personnel.

The system of the present invention provides the measurement of the containment gases necessary for a safe cooling down of the reactor after a loss of coolant accident has occurred.

At the present time, governmental regulations require that all nuclear generator power plants have the containment gas monitored to determine the amount of hydrogen present. Some power generating plants monitor both the amount of hydrogen and oxygen in the containment gas mixture.

The monitoring system of the present invention can, without attention, continuously monitor the containment gas of a boiling water reactor or a pressurized water reactor handling pressures from zero to 60 pounds per square inch gauge on the inlet and discharging to the same pressures. Containment gas samples having temperature ranges between 50° F. and 300° F. and relative humidity from zero to 100 percent are accommodated. The monitoring system is operative on the basis of continuously obtaining a portion or sample of the containment gas and conveying it out of the pressure vessel 11 to a gas analyzer cabinet 12 by means of a conduit insulated or heated to maintain the sample in the steam phase.

The analyzer cabinet 12 is constructed and defined for monitoring and analyzing the quantity of the preselected known gases in the containment gas mixture. The analyzer cabinet 12 basically includes two sections or subsystems. A subsystem 12A is identified as a containment gas sample conditioning system, while the system 12B is identified as a containment gas sample measuring system. Both the conditioning system 12A and the measuring system 12B are maintained within a heated compartment 13 arranged within the cabinet 12. The heated compartment 13 is provided to maintain a sample flowing through the systems 12A and 12B at a temperature on the order of 300° F. The containment gas sample may be conveyed from the pressure vessel 11 to the cabinet 12 by means of an insulated conduit 14 for maintaining the sample in the steam phase. The gas sample enters the cabinet 12 at a point outside the heated compartment 13 from where it is conveyed into the gas sample conditioning system 12A as diagrammatically illustrated in FIG. 1. In the gas sampling conditioning system 12A, a small portion of the gas, on the order of one percent of the containment gas sample, is separated out and conveyed by means of a conduit 15 to the measuring system 12B. The remaining major portion of the gas sample is conveyed out of the heated compartment 13 and cooled to a temperature below 150° F. prior to being returned to the pressure vessel 11. The separated portion of the gas sample to be measured is conveyed through the measuring system 12B, and after it is analyzed it is conveyed by means of a conduit 16 to be recombined with the unmeasured cooled portion of the containment gas sample from the system 12A. The entire gas sample is returned to the vessel 11 by means of a conduit 17 coupled between the cabinet 12 and the pressure vessel 11.

An important feature of the system is the achievement of a constant mass flow of the gas mixture, independent of the gas sample pressure, in a manner to prevent steam condensation and erratic mass flow of the gas. This results through the provision of the heated compartment 13 and arrangement of an outlet flow control valve within the compartment while maintaining a constant differential pressure between the inlet and outlet to the analyzer cabinet 12.

An important consideration in the implementation of the monitoring system of the type of the present invention is the type of gas sensor employed in the system. The usual sensors employed for sensing hydrogen and oxygen are difficult to apply due to the rapid and extreme changes that may result in the pressure, temperature and composition of the containment gas. The present invention utilizes a gas sensor of the thermal conductivity type since it is insensitive to pressure and temperature and is not affected by vibration or radiation and may be readily adapted for the purposes of the present system. The thermal conductivity cell is capable of satisfactory operation under the conditions that prevail in the containment gas before, during, or after a loss of coolant accident. The thermal conductivity cells of the type utilized in the monitoring system are commercially available and one such cell is available from Comsip Delphi, Inc. of El Monte, Calif. Similar cells are commercially available from other manufacturers.

A thermal conductivity cell is generally arranged in an electrical bridge network and such cells have been used heretofore for measuring gases such as hydrogen in a gas mixture. There was no known use of such a cell prior to the disclosure in this application in the manner in which it is employed in the present gas monitoring system. A thermal conductivity cell section comprises a self-heating filament arranged in the center of a temperature controlled metal cavity. The filament temperature is determined by the power dissipated in the filament, the cavity wall temperature and the heat conducted from the filament to the cavity walls by the gas in the cavity. Thermal conductivity varies with gas species thereby causing the filament temperature to change as the gas, or gases, introduced into the cavity changes. The electrical resistance of the self-heating filament changes the temperature and therefore affects the electrical balance condition of any electrical bridge network it is connected into. A measurement of the gas conveyed through the thermal conductivity cell can be accomplished by using a thermal conductivity cell having two sections with independent self-heating filaments. Each filament is arranged in a separate cavity and each is connected in an arm of an electrical bridge network. The electrical bridge thus defined may be normally arranged in a balanced bridge condition so that any differences in thermal conductivity of the gas, or gases, that are conveyed through the separate cavities are signalled electrically by sensing any unbalance condition. Despite the fact that the thermal conductivity cell technique is not specific, it is extremely reliable when the gas or the gas mixtures that are conveyed through the cell are known and the variation in the composite thermal conductivity can be accurately determined. The electrical bridge may be initially balanced, or an electrical zero may be defined by first introducing the same gas to both metal cavities and then adjusting the filaments so that they operate at the same temperature. Any difference in the gases that are conveyed through the two individual cavities will be detected due to the unbalancing of the bridge resulting in the production of an output signal that increases with increasing differences in thermal conductivity of the gas conveyed.

Figure 3:
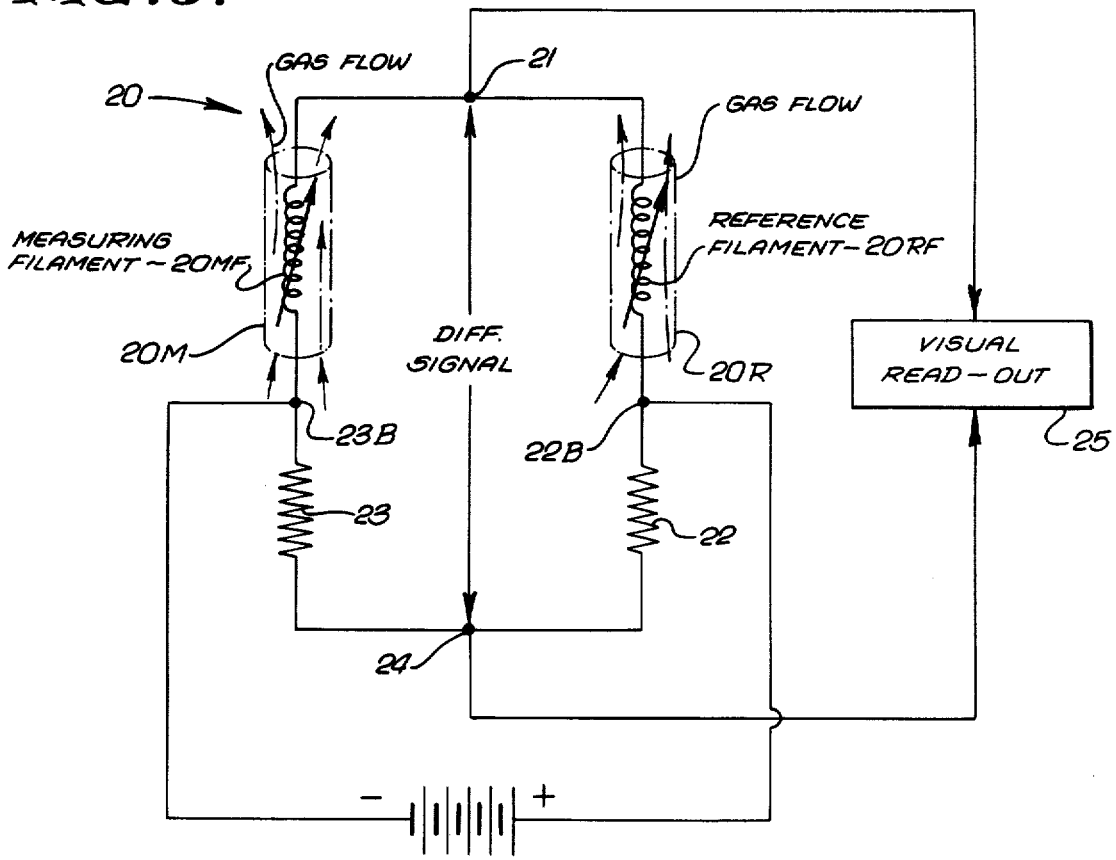
FIG. 3 is a schematic illustration of the electrical arrangement of the filaments of the thermal conductivity cell in an electrical bridge network in accordance with the system of FIG. 2.

Now referring to FIG. 3, the diagrammatic representation of the thermal conductivity cell arranged in an electrical bridge network will be examined in detail. The thermal conductivity cell 20 is defined as comprising a reference cavity 20R and a measuring cavity 20M. The reference cavity 20R has fixed therein a reference filament 20RF substantially centrally thereof. The measuring filament 20MF is similarly arranged in the measuring cavity 20M. Both filaments vary in resistance with the changes in temperature resulting from the differences in the thermal conductivity of the gases conveyed through the cavities 20R and 20M. One end of each filament 20RF and 20MF is connected together to define one junction of the electrical bridge network or the junction 21 illustrated in FIG. 3. The remaining end of the reference filament 20RF is connected to a fixed resistor element 22 arranged in another arm of the bridge network. Similarly, a fixed resistor 23 is connected to the remaining end of the filament 20MF in another arm of the bridge network. The values of the resistors 22 and 23 may be identical. The remaining ends of the resistors 22 and 23 are connected together and form a junction 24 of the bridge circuit. The DC source for the bridge network is coupled to the junctions 22B and 23B arranged intermediate the resistors 22 and 23 and filaments 20RF and 20MF respectively. The balanced condition, or any unbalance of the bridge network is sensed by means of a visual readout device 25 connected between the junctions 21 and 24. The output of the readout device 21 may be calibrated to read in any convenient manner. The temperature of the cavities 20R and 20M are controlled precisely so as to provide the necessary accuracy in measuring the components of the gas conveyed therethrough.

This measuring system takes advantage of the fact that the different gases have different thermal conductivity properties. For the purposes of measuring or sensing the gas in the containment gas, it is known that the thermal conductivity of hydrogen is approximately seven times higher than nitrogen, oxygen and water vapor. These latter-mentioned gases have nearly identical thermal conductivity. This allows hydrogen gas to be measured in the presence of these other gases, all mixed in the containment gas. Accordingly, by conveying the gas sample past one filament (the reference filament 20RF), modifying the constituency of the gas sample by removing the hydrogen and then conveying it past the other filament (the measuring filament 20MF) after the gas is modified, in either the serial or parallel arrangement, the measurement of the quantity of the preselected gas (hydrogen) may be accomplished. Under these conditions, any significant change in sample constituency due to the catalytic reaction is indicated by a difference in thermal conductivity of the sample at the two cavities and is measured by the two filaments 20RF and 20MF of the cell 20. The visual readout senses this difference as an unbalanced bridge condition and can be calibrated to indicate the quantity of (1) oxygen in the presence of excess hydrogen (2) reacted water vapor or (3) hydrogen in the presence of excess oxygen.

Now referring to FIG. 2, the monitoring system of the present invention will be described as it may be embodied for measuring the amount of hydrogen gas in the containment air sample utilizing the thermal conductivity cell 20 of FIG. 3. The thermal conductivity gas analyzing cell 20 will be considered as having a reference section and a measuring section as described in conjuction with FIG. 3. The two sections of the gas analyzer 20 are merely illustrated as the filaments 20RF and 20MF for simplicity of illustration but are considered to be connected into an electrical bridge network and coupled to the indicator 25 as described hereinabove. The gas analyzer 20 is arranged in the heated compartment 13 along with the other control components for maintaining all components of the gas sample in the vapor state resulting in a measuring accuracy not heretofore achieved. The heated compartment 13 is arranged within the analyzer cabinet 12. The temperature for the compartment 13 is selected to maintain the temperature of the gas sample above the saturation temperature of the gas sample. Typical temperatures for the compartment may be 275° to 300° Fahrenheit. The flow control components are maintained in the heated compartment to maintain a continuous mass flow of the sample through the measuring system.

A heated sample to be measured is coupled to the analyzer cabinet 12 through an entry valve 30 which may be coupled to the conduit 14 for receiving the heated sample from the containment pressure vessel 11. The valve 30 is arranged outside of the heated compartment 13 and is the isolation valve for the sample flow to the heat sink 31 arranged within the compartment 13. The heat sink or heat exchanger 31 is provided to assure that the sample is essentially at the same temperature as the temperature of the heated compartment 13. From the heat sink 31, the gas sample is conveyed to a moisture separator 32 also arranged within the heated compartment 13. The moisture separator 32 is essentially a moisture trap that separates out any moisture in the gas sample to prevent it from inadvertently being conveyed to the gas analyzer 20. At the moisture separator 32, a small portion (on the order of one percent of the gas sample) is separated out and conveyed by means of a conduit 33 to the gas analyzer 20 for measuring purposes. The remaining portion of the gas sample is not analyzed and is conveyed along with any moisture out of the heated compartment 13 from the moisture separator 32 by means of the conduit 34 and a by-pass valve 35. The by-pass flow through the valve 35 has two purposes (1) to eliminate any water that may have condensed in the sample lines between the containment vessel 11 and the analyzing system circuit 12 and (2) to decrease the delay time of response by pumping as much gas through the sample lines as possible. After the unmeasured portion exits from the heated compartment 13, it flows to an air cooled heat exchanger 36. The air cooled heat exchanger 36 is arranged outside of the heated compartment 13 and cools the unmeasured portion of a gas sample to a temperature below 150° Fahrenheit. This portion of the air sample is conveyed by means of the conduit 27 back to the pressure vessel 11, as will be more evident hereinafter.

The small portion of the gas sample to be measured or analyzed is conveyed within the heated compartment 13 by means of a conduit 33 to a heat sink 38 immediately prior to being conveyed through the reference section of the gas analyzer 20. After passing through the reference section of the gas analyzer 20, the gas sample flows through a one-way check valve 39 and a catalytic reactor 40 arranged in serial fashion as illustrated. After the gas sample to be measured exits from the catalytic reactor 40 it flows through a second one-way check valve 41 and is coupled by means of a conduit 42 to a heat sink 43 immediately prior to being conveyed through the measuring section of the gas analyzer 20. From the measuring section of the gas analyzer 20, the gas is conveyed by means of a conduit 44 to a flow control valve 45. The flow control valve 45 is also maintained within the heated compartment 13 for the purposes of maintaining a constant mass flow through the measuring system. After the gas has been measured, it exits from the heated compartment 13 through the flow control valve 45 and is conveyed by means of the conduit 46 to a back pressure regulator 47. The back pressure regulator 47 is arranged with a flow control valve 45 to maintain a constant mass flow through the system. A differential pressure switch 48 is coupled between the conduit 46 and the pressure sensing line 49 coupled between the back pressure regulator 47 and the entry side of the valve 45 and is utilized as a flow alarm. From the back pressure regulator 47 the analyzed gas sample flows by means of the conduit 49M to the junction of the conduit 37 wherein it is recombined with the unmeasured portion of the gas sample. The entire gas sample is then conveyed by means of the conduit 50 out of the analyzer cabinet 12 through to the back pressure regulator 51. The back pressure regulator 51 has one input coupled to the conduit 50 and a pressure line 52 coupled to the entry conduit for the system outside of the heated compartment 13 at a point between the flow control valve 30 and the heat sink 31. The back pressure regulator 51 provides a constant pressure differential across the sections of the cell 20. The exit of the pressure regulator 51 is coupled to a gas sample pump 52 for pumping the gas sample out of the cabinet 12 through an isolation valve 53. The output of the isolation valve 53 may be coupled to the conduit 17 for returning the gas sample to the containment pressure vessel 11.

In this arrangement, it should be noted that the gas analyzer 20 and the catalytic reactor 40 are maintained in the heated compartment 13 along with the flow control valve 45. This arrangement maintains a constant mass flow through the measuring system for any combination of the quantity of steam and nitrogen. By using thermal conductivity which, to a first approximation, is independent of pressure, the entire measurement system is permitted to float up and down relative to the pressure of the containment gas without affecting the accuracy of the measurement. To this end, all of the differential pressure regulators 47, 51, 56 and 63 are connected into the system as flow controllers. The regulator 47 maintains a preselected pressure drop across the valve 45. The regulator 51 maintains a desired pressure drop across the valve 35. Similarly, the regulator 56 and the valve 56V control the flow of the hydrogen span gas. The regulator 63 and the valve 63V control the flow of the reagent gas flow, or the hydrogen gas to be added to the containment sample as illustrated in FIG. 2. The pressure of the gases added to the system must be approximately 20 pounds per square inch gravity above the maximum pressure of the containment gas; as noted hereinafter, this is 80 P.S.I.G. The outlet pump 52 may be operated at maximum capacity only if the valve 35 is throttled down just enough to provide an adequate pressure drop to make the regulator 51 just start to work.

With the above structure in mind, the operation of the measuring system for analyzing the quantity of hydrogen gas within the gas sample will be examined. It will be initially assumed that the gas analyzer 20 has been specifically calibrated for this purpose and which calibration procedure will be explained more fully hereinafter. It should now be appreciated that the heated containment gas sample from the pressure vessel 11 is conveyed to the analyzer cabinet 12 and is received at the isolation valve 30. The gas sample then flows into the heated compartment 13 entering the heat sink 31 and from this point the gas sample is conveyed through the moisture separator 32. The bulk of the gas sample, or approximately 99 percent, flows through the moisture separator and out of the heated compartment by means of the conduit 34 and the flow control valve 35 (both arranged within the heated compartment 13) to the air cooled heat exchanger 36 arranged outside of the compartment 13. At the heat exchanger 36, the gas is cooled to below 150° F. and conveyed by means of the conduit 37 for return to the pressure vessel 11 along with the separated portion of the gas sample. The remaining portion, or approximately one percent, of the gas sample is conveyed to the gas analyzer 20 arranged within the heated compartment 13. The sample to be measured is conveyed by means of the conduit 33 to the heat sink 38 and through the reference section of the gas analyzer 20. From the reference section, the gas is conveyed through the check valve 39 to the catalytic reactor 40 and the check valve 41 to the heat sink 43. The gas, as it is conveyed to the catalytic reactor 40, is constituted as it appears in the containment pressure vessel 11. At the catalytic reactor 40, free oxygen is catalytically recombined with hydrogen to form water vapor. This modified gas sample is then conveyed through the one-way check valve 41, heat sink 43 and then through the measuring section of the gas analyzer 20 as illustrated in FIG. 2. In flowing through the measuring section, the modified gas sample flows adjacent the measuring filament 20MF so that the change in the composition of the gas sample is sensed by the difference in thermal conductivity produced by the change in hydrogen content signalled as a difference in electrical resistance as measured by both the reference and measuring sections of the thermal conductivity cell 20. This unbalance bridge condition is signalled by the visual indicator 25 which can be calibrated to indicate reacted hydrogen.

It should now be noted that if an excess amount of oxygen does not exist in the gas sample as it is conveyed from the pressure vessel 11 for recombining all of the hydrogen, oxygen may be added thereto in accordance with the present system immediately prior to conveying the sample to be measured to the analyzer 20. The amount of oxygen that is added is determined by the highest range of the gas analyzer 20. It will, of course, be appreciated that with no gases being added to the air sample, the indicator 25 will indicate only the total reaction concentration of hydrogen and oxygen.

For the purpose of calibrating the analyzing system, span calibration is accomplished by introducing a known amount of oxygen and a gas mixture of hydrogen in nitrogen to the thermal conductivity cell 20. This will provide a specific output for readout calibration. As illustrated in FIG. 2, the hydrogen span gas may be coupled to the system at the coupling element S and conveyed through shut-off valve 54. The hydrogen span gas may be provided at 80 P.S.I.G. The shut-off valve 54, which may be solenoid operated, is coupled by means of the conduit 55 to the differential pressure regulator 56 arranged in a serial flow path with the valve 56V for controlling the flow of span gas. From the valve 56V, the gas flows by means of the conduit 57 through the one-way check valve 58. From the check valve 58, the gas flows by means of the conduit 59 to an input for the capillary tubing 60 arranged intermediate the ends thereof. The span gas flow controller is set to permit the span gas flow to be in excess of the flow permitted by the controller 51 for the flow of gas to be analyzed. This causes the span gas flow to split in the capillary tubing 60 with a portion flowing to the gas sensor 20 and a portion reversing the flow in conduit 33 to assure that only the span gas and the reagent gas reaches the gas sensor 20. Similarly, the hydrogen reagent air may be coupled to the point R and conveyed through a solenoid operated calibration valve 61. The reagent air may also be provided at 80 P.S.I.G. A conduit 62 couples the reagent air from the calibration valve 61 to a flow controller comprising the regulator 63 and the valve 63V. The output of the thus defined flow controller coupled by means of the conduit 64 by means of a check valve 64V to the exit end of the capillary tubing 60 where it is mixed with the span gas and flows to the sensor 20. In addition, there is provided for calibration purposes another solenoid operated calibration valve 65 having its input coupled to the conduit 62 intermediate the calibration valve 61 and the regulator 63. The output of the calibration valve 65 is coupled to a conduit 66 for conveying the operating air to a pneumatically operated calibration valve 67. The calibration valve 67 is arranged in a path for by-passing the catalytic reactor 40 and is coupled at the exit of the sensor ahead of the input to the check valve 39 to cause the air sample to flow through the open calibration valve 67. From the calibration valve 67, the air sample is coupled by means of the conduit 68 to flow directly into the heat sink 43 by means of the conduit 42.

With the above described structure, zero calibration is accomplished by causing the gas to flow unchanged through both sections of the thermal conductivity cell 20. This is accomplished by either by-passing the catalytic reactor 40, or introducing pure hydrogen into the system instead of the span gas. It should now be appreciated that with the same gas mixture flowing through both sections of the cell 20 that the thermal conductivity of the gas to the filaments 20RF and 20MF will be the same. The bridge circuit may be externally adjusted to achieve a balanced condition as the unmodified gas passes through both sections of the gas sensor 20. This will cause the electrical bridge network to be balanced and the electrical output provided at the indicator 25 will be defined to be zero.

Now referring to FIG. 4 wherein a system is illustrated where both the quantity of hydrogen and oxygen in the containment air may be continuously monitored, either simultaneously or separately. The structure for measuring the oxygen content of the air sample is essentially identical to that described in FIG. 2 for solely measuring the hydrogen of the containment air sample. The elements that are common with regard to the oxygen analyzing section bear the same reference numerals as in the hydrogen analyzing section with the suffix "-0" added. The oxygen analyzing system is arranged in a parallel flow path with respect to the air sample to be measured as it is derived from the moisture separator 32. Accordingly, the air sample portion separated out at the element 32 is conveyed also to the corresponding heat sink 38-0. The same elements are utilized and the same technique is utilized for measuring the oxygen content except that an excess amount of hydrogen must be continuously supplied to the analyzing element to assure the complete reaction of all of the available oxygen at the reactor 40-0.

As illustrated in FIG. 4, the oxygen reagent, hydrogen is coupled at the point "R-O" and conveyed to the measuring system through a solenoid operated shut-off valve 70, and from the valve 70 through a pressure regulator 71. The pressure regulator 71 in combination with the valve 71V function as a flow controller for the reagent gas. From the valve 71V the reagent gas flows through a one way check valve 72V and is conveyed by means of the conduit 72 to the input side of the heat sink 38-0. This allows the hydrogen to be conveyed through the reference section of the analyzer 20-0 in combination with the gas sample to be measured and assures that a sufficient amount of hydrogen is present to completely react out the oxygen available in the gas sample at the catalytic reactor 40-0. This hydrogen supply is continuously supplied to the gas sensor 20-0 when it is desired to monitor the oxygen content of the containment gas sample. Span calibration is provided by coupling the oxygen span gas to the point S-0 to the capillary 60-0 as in the previous embodiment. The catalytic reactor by-pass is provided by the valve 67-0 controlled through the conduit 66-0 coupled to the conduit 66 in parallel relationship as illustrated in FIG. 4.

The measured gas sample flows from the oxygen gas analyzer 20-0 and out of the heated compartment 13 by means of the flow control valve 45-0 to be combined with the portion of the gas sample from the hydrogen gas analyzer 20 and the unmeasured portion of the gas sample. The three portions of the remixed gas flows through the regulator 51 and by means of the sample pump 52 is conveyed back through the isolation valve 53 to the containment vessel 11. The regulator 51 maintains a constant differential pressure between the input and exit of the system of approximately 6 lbs. to aid in maintaining the constant mass flow through the entire system of FIG. 4.

In the analysis of the oxygen content of the containment gas sample, an excess amount of hydrogen is continuously supplied to the oxygen sensor 20-0. This may be on the order of 25 percent more hydrogen than required for reacting out the oxygen. A small portion, on the order of 4 percent, of the excess hydrogen is utilized to convert the oxygen to water vapor at the catalytic reactor 40-0. The remaining portion (21 percent) is utilized in the measuring section of the cell 20-0 for generating the electrical signal resulting from the catalytically modified air sample. This again takes advantage of the difference in thermal conductivity of hydrogen with respect to the other gases mixed therewith in the containment gas sample, as described hereinabove.

Now referring to FIG. 5 wherein a measuring system is illustrated with the thermal conductivity cell sections arranged in a parallel flow path instead of the series flow arrangement utilized in FIGS. 2 and 4. The analyzing system is the same as described hereinabove with the exception of the parallel arrangement of the thermal conductivity cell sections.

As illustrated in FIG. 5, the gas sample to be measured enters the gas analyzer 20 through a heat sink and flame arrestor 80. At the exit end of the arrestor 80, the gas flow is split so as to flow through both arms each containing one of the filaments 20RF and 20MF. The left-hand parallel conduit 81 conveys the gas sample past the reference filament 20RF in unmodified form and out of the reference cell section by means of the exit conduit 82. The catalytic reactor 40 is arranged in the right-hand parallel conduit 83 in a series flow path with the measuring filament 20MF. The modified gas sample exiting from the reactor 40 flows out of the measuring cell section by means of an exit conduit 84. The split gas sample is recombined and flows to the flow control valve 45 through a second flame arrestor 85. From the flow control valve 45, the gas flows out of the heated compartment 13 and is recombined with the unmeasured portion of the gas sample as in the previous embodiments.

This parallel flow arrangement of the gas to be measured has been found to be advantageous over the serial flow arrangement as the dynamic response is better.

All of the components employed for the above-described monitoring system are commercially available. The components have been selected on the basis of their physical characteristics in view of the environment to which they are subjected. To this end, the elastomers that are substituted into the standard components are selected on the basis of their resistance to radiation and heat, for example.

What is claimed is:

1. Apparatus for continuously monitoring and signalling the quantity of a preselected gas in a mixture of gases from a nuclear reactor pressure vessel comprising
 a compartment maintained at a preselected temperature,
 gas inlet means located outside of the compartment for continuously receiving a sample of gas to be monitored from a gas sample source and continuously conveying the sample to said compartment so as to continuously maintain the gas sample at said preselected temperature, while being conveyed through said compartment to thereby maintain the concentration of the mixed gases of the gas sample source,
 means located within the compartment for continuously receiving the gas from the inlet means and for continuously separating out a relatively small portion of the gas sample for measurement purposes,
 thermal conductivity gas sensing means arranged within said compartment for continuously measuring and signalling the quantity of a preselected, known gas in the gas sample,
 means for continuously conveying said small portion of the gas sample to said sensing means,
 catalytic reaction means arranged within said compartment for continuously altering one of the gas constituents in the gas sample conveyed therethrough,
 means for continuously conveying said small portion of the gas sample to said reaction means.
 means for continously conveying the reacted, sensed gas from said reaction means through said sensing means,
 means arranged within said compartment for continuously receiving the small portion of measured gas from said sensing means for maintaining a substantially constant mass flow of gas through said sensing means,
 means for continuously rendering said sensing means independent of the pressure of the gas received from said source,
 means arranged outside of said compartment for cooling gas, and
 means for continously conveying the remaining portion of the unmeasured gas from said separation means to the gas cooling means, and gas outlet means for continuously combining and conveying the cooled gas with the measured gas portions received from the constant mass flow control means for continuous conveyance back to the gas sample source.

2. Apparatus for continuously monitoring and signalling the quantity of a preselected gas in a mixture of gases as defined in claim 1 wherein said gas sensing means comprises a pair of gas sensing means for individually sensing a different, known gas in the gas sample.

3. Apparatus for continuously monitoring and signalling the quantity of a preselected gas in a mixture of gases as defined in claim 2 wherein one of said gas continuously senses means sensing the oxygen, content of the gas sample and the other gas sensing means continuously senses the hydrogen content of the gas sample.

4. Apparatus for continuously monitoring and signalling the quantity of a preselected gas in a mixture of gases as defined in claim 1 including means arranged with said outlet means for continuously maintaining a pressure differential between said inlet and outlet means.

5. Apparatus for continuously monitoring and signalling the quantity of a preselected gas in a mixture of gases as defined in claim 1 including gas pumping means arranged between the outlet end of the outlet means and said pressure differential means.

6. Apparatus for continuously monitoring and signalling the quantity of a preselected gas in a mixture of gases as defined in claim 1 wherein the compartment is maintained at a temperature for preventing the condensation of any steam present in the gas sample while being conveyed therein and thereby prevent altering the gas content of the sample.

7. Apparatus for monitoring and signalling the quantity of a preselected gas in a mixture of gases as defined in claim 3 wherein said oxygen gas sensing means includes means for continuously supplying a preselected quantity of hydrogen gas to said sensing means in combination with the gas sample to thereby cause the oxygen in the sample to be reacted out at said reaction means with a portion of the supplied hydrogen.

8. Apparatus for monitoring and signalling the quantity of a preselected gas in a mixture of gases as defined in claim 1 wherein said gas sensing means comprises means for defining temperature controlled cavities to permit a gas to flow therethrough and an individual self-heating filament arranged in each of the cavities for responding to the heat energy conducted by the gas sample.

9. Apparatus for monitoring and signalling the quantity of a preselected gas in a mixture of gases as defined in claim 8 wherein said filaments are arranged in separate arms of an electrical bridge circuit and the bridge circuit is initially maintained in a balanced bridge condition, and including means for signalling an unbalanced bridge condition resulting from a gas sample having different gases mixed therein.

10. Apparatus for monitoring and signalling the quantity of a preselected gas in a mixture of gases as defined in claim 9 wherein said gas sensing means is a hydrogen gas sensing means and the reaction means converts the hydrogen in the sample conveyed therethrough to water vapor.

11. Apparatus for monitoring and signalling the quantity of a preselected gas in a mixture of gases as defined in claim 9 including means for conveying the same, unmodified, gas past each filament of the gas sensing means and
 means for adjusting the bridge circuit when the same gas is conveyed past the filaments for defining a balanced bridge condition.

* * * * *